United States Patent [19]

Ales et al.

[11] Patent Number: 4,726,873
[45] Date of Patent: Feb. 23, 1988

[54] APPARATUS FOR APPLYING CONTOURED ELASTIC TO A SUBSTRATE

[75] Inventors: Thomas M. Ales; Jeffrey J. Samida, both of Neenah; Donald F. Arthur; Ronald H. Wideman, both of Menasha, all of Wis.

[73] Assignee: Kimberly-Clark Corporation, Neenah, Wis.

[21] Appl. No.: 791,885

[22] Filed: Oct. 28, 1985

[51] Int. Cl.$^4$ .............................................. B29C 55/06
[52] U.S. Cl. ...................................... 156/495; 269/20; 156/518; 156/519; 156/521; 156/530; 156/552; 156/560; 425/346; 425/390; 425/417; 425/418; 425/DIG. 44
[58] Field of Search ............... 156/495, 518, 519, 515, 156/251, 265, 560, 229, 160-161, 164, 169, 173-174, 176, 289, 302-303, 496, 521, 530, 543, 545, 552, 580; 604/385.2, 396; 128/165-166.5, 169; 269/292-295, 20; 264/313; 425/389-390, DIG. 44, 417, 418, 346, 348, 237; 249/65

[56] References Cited

U.S. PATENT DOCUMENTS

| | | |
|---|---|---|
| 2,402,074 | 6/1946 | Nield . |
| 2,957,792 | 10/1960 | Magid . |
| 2,976,199 | 3/1961 | Rand . |
| 3,245,407 | 4/1966 | Mason . |
| 3,466,359 | 9/1969 | Van Burleigh et al. . |
| 3,604,015 | 9/1971 | Dove . |
| 3,644,157 | 2/1972 | Draper . |
| 3,663,962 | 5/1972 | Burger . |
| 3,756,878 | 9/1973 | Willott . |
| 3,828,367 | 8/1974 | Bourgeois ............................ 156/164 |
| 4,033,801 | 7/1977 | Gros . |
| 4,227,952 | 10/1980 | Sabee . |
| 4,236,954 | 12/1980 | Edwards . |
| 4,297,157 | 10/1981 | Van Vliet . |
| 4,371,417 | 2/1983 | Frick et al. . |
| 4,394,787 | 12/1983 | Radzias . |
| 4,418,123 | 11/1983 | Bunnelle et al. . |
| 4,479,836 | 10/1984 | Dickover et al. . |
| 4,488,923 | 12/1984 | Pieniak . |

Primary Examiner—Donald E. Czaja
Assistant Examiner—Merrell C. Cashion
Attorney, Agent, or Firm—Paul A. Leipold; Donald L. Traut; Jeremiah J. Duggan

[57] ABSTRACT

This invention is generally accomplished by providing continuous self-adhesive strands of elastic to a substrate having retractable supports extending therefrom. The retractable supports in a convex pattern are contracted with the self-adhering elastic and the substrate bearing the elastic and supports is brought into contact with the web to which the elastic is to be transferred. The series of supports around which the elastic contacts are forced to retract as the self-adhering elastic is pressed against the web causing the elastic to transfer to the substrate thereby creating an elastic band on the substrate. In a preferred form the substrate is fed two strips of self-adhering elastic that are applied on each side of a series of a convex pattern of pins and then pressed together around opposing sides of the convex pattern of pins to seal the elastic to itself and sever the elastic, creating a contoured closed loop around the pins.

17 Claims, 20 Drawing Figures

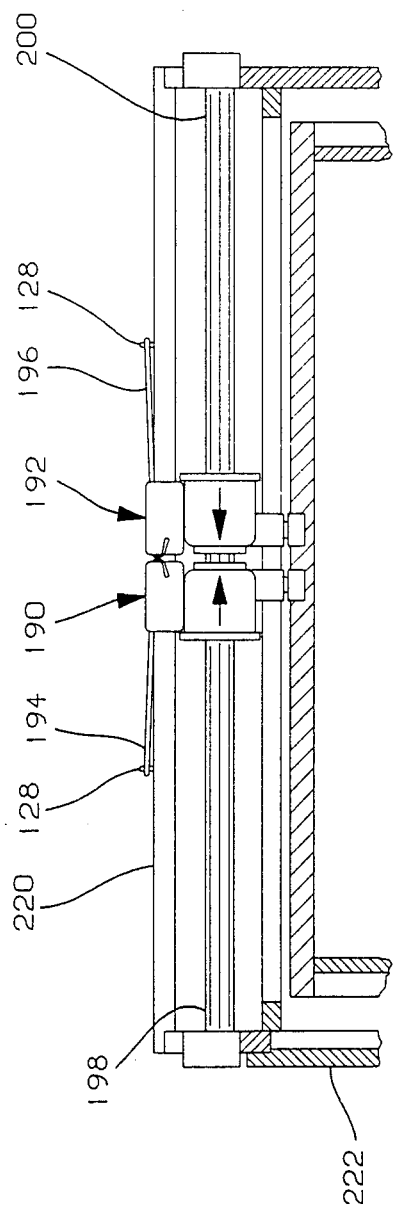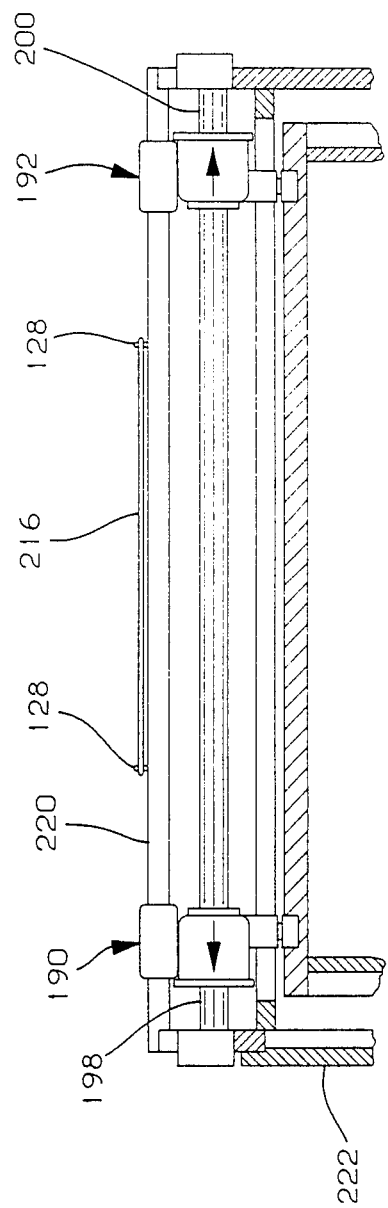

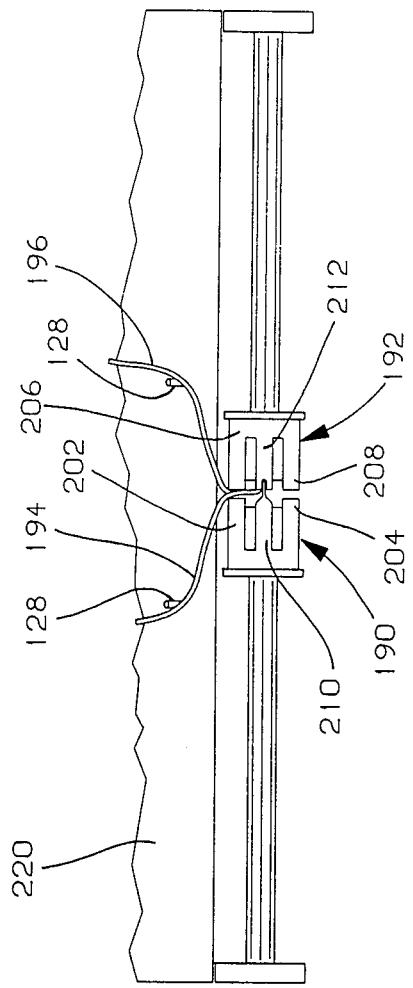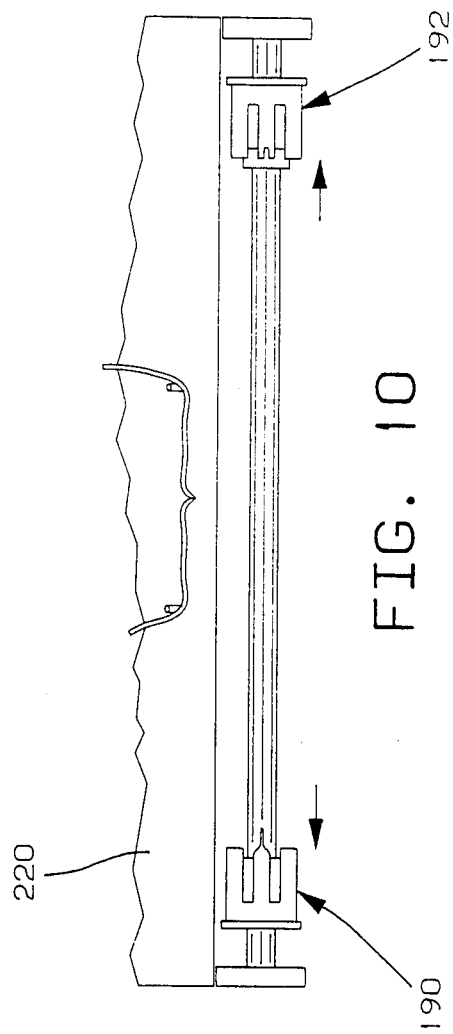

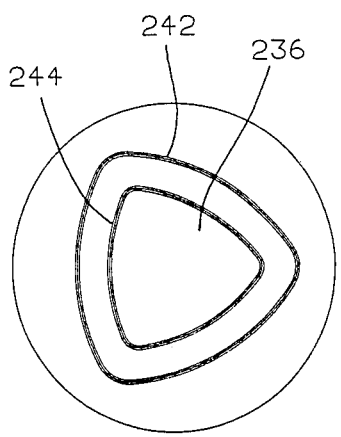
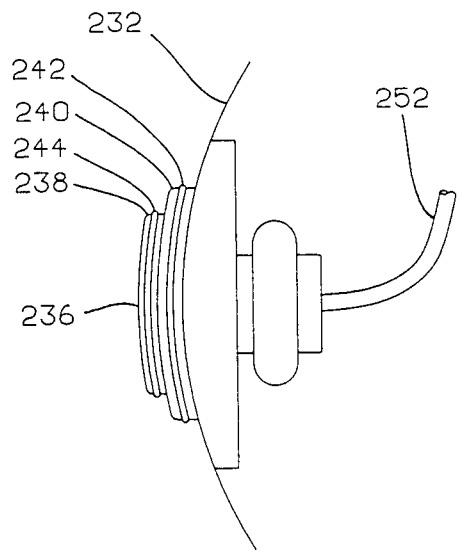
FIG. 12　　FIG. 13
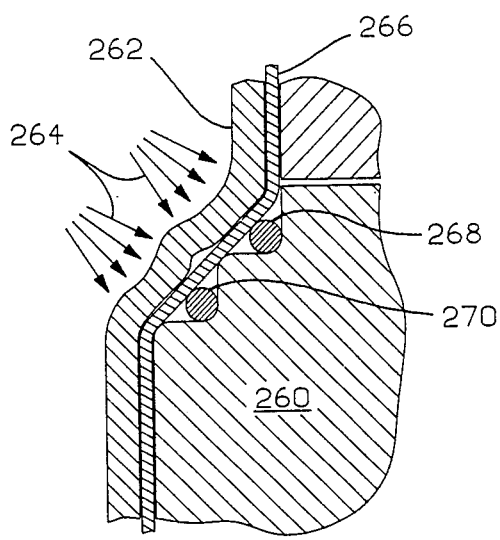
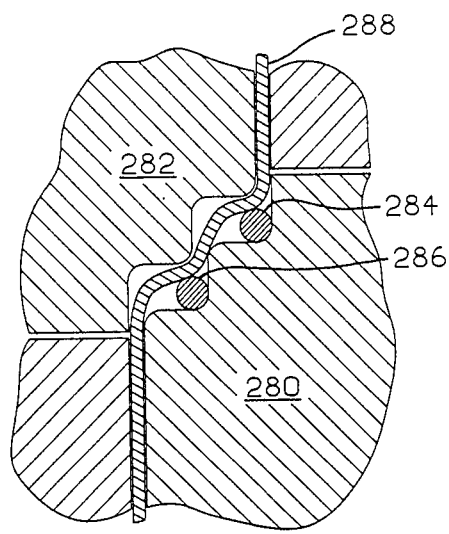
FIG. 14　　FIG. 15

APPARATUS FOR APPLYING CONTOURED ELASTIC TO A SUBSTRATE

TECHNICAL FIELD

This invention relates to a method and apparatus for application of self-adhering elastic material to a substrate. In particular, the invention relates to the formation of disposable garments utilizing contoured elastics.

BACKGROUND ART

In U.S. Pat. No. 4,418,123—Bunnelle et al., an extrudable self-adhering elastic is disclosed. It is disclosed therein that the material may be utilized to provide elasticity to disposable garments by stretching the material and applying it to a deformable substrate. This material has been difficult to utilize in high-speed formation of diapers and other disposable garments as when it is stretched it will not adhere well to polymer substrates without pressure being applied to the material as it is applied to the substrate. Further, there has been no practical way of applying the material in contoured patterns such as circular patterns onto the deformable substrates. It is desirable that elastic be contoured for use in disposable garments such as diapers, face masks and disposable hats.

It is known in the formation of disposable diapers that elastic may be applied to the diaper to form elasticized areas at the legs and at the waist. However, as illustrated in U.S. Pat. Nos. 4,227,952—Sabee, 4,050,462—Woon et al., and in 3,860,003—Buell, the placement of elastics is ordinarily in straight lines. There has been proposed in U.S. Pat. No. 3,828,367—Bourgeois, a method of forming elastics on disposable clothes by placing the elastic into grooves in a roller from which it is applied to the garment.

There remains a need for a method and apparatus for applying curved elastic easily to a continuous web. There also particularly is a need for a method of accurately applying generally circular self-adhering elastic to substrates.

DISCLOSURE OF THE INVENTION

It is an object of this invention to overcome disadvantages of prior processes and apparatus.

It is another object of this invention to reliably place self-adhering elastic onto a substrate.

A further object of this invention is to provide more accurate placement of elastic on substrates.

Another object of this invention is to provide a continuous process for formation of curved and generally circular elastics.

These and other objects of the invention are generally accomplished by providing continuous self-adhesive elastics to a substrate having retractable supports such as a pattern of pins. The retractable supports are placed in contact or looped with the self-adhering elastic, and the substrate bearing the elastic in contact with the supports is brought into contact with a web to which the elastic is to be transferred. The series of supports in contact with the elastic are forced to retract as the self-adhering elastic is pressed against a web causing the elastic to transfer to the web, thereby creating an elasticized band on the web.

In a preferred form the substrate is fed in a straight line, two strips of self-adhering elastic that are applied on each side of a series of a generally convex polygonal pattern of pins and then pressed together and bonded at opposing sides of the patterned pins to seal the elastic to itself. The elastic is severed in the sealed area thereby creating contoured shapes around the pins as the elastic loops contract around the pattern of pins.

BRIEF DESCRIPTION OF THE DRAWINGS

FIGS. 7 and 8 are cross-sectional views on cross section lines 7 and 8 of FIG. 6.

FIG. 9 is a top view of FIG. 7.

FIG. 10 is a top view of FIG. 8.

FIGS. 12 and 13 illustrate the molds used for transfer of loops of elastic material from an inflatable male mold the roll carrying a web.

FIG. 14 is a partial cross section illustration of transfer of elastics from a rigid male mold to a flexible female mold bearing a web of material.

FIG. 15 illustrates transfer of elastic utilizing rigid male and female molds.

MODES FOR CARRYING OUT THE INVENTION

The method and apparatus of the invention has many advantages over previous systems for elastic application particularly for self-adhering elastic. The system of the invention allows accurate registration of the elastic with the substrate. The invention allows the simple straight line feeding of elastic to result in convex polygonal shapes of contoured elastic on a substrate for transfer to a web. The invention further provides positive pressure bonding of the self-adhering elastic to the web, thereby minimizing the chance of the elastic not bonding to the web. The superior registration of the system of the invention allows more accurate sizing of products to be formed. These and other advantages will be apparent from the description below.

Figure 1:
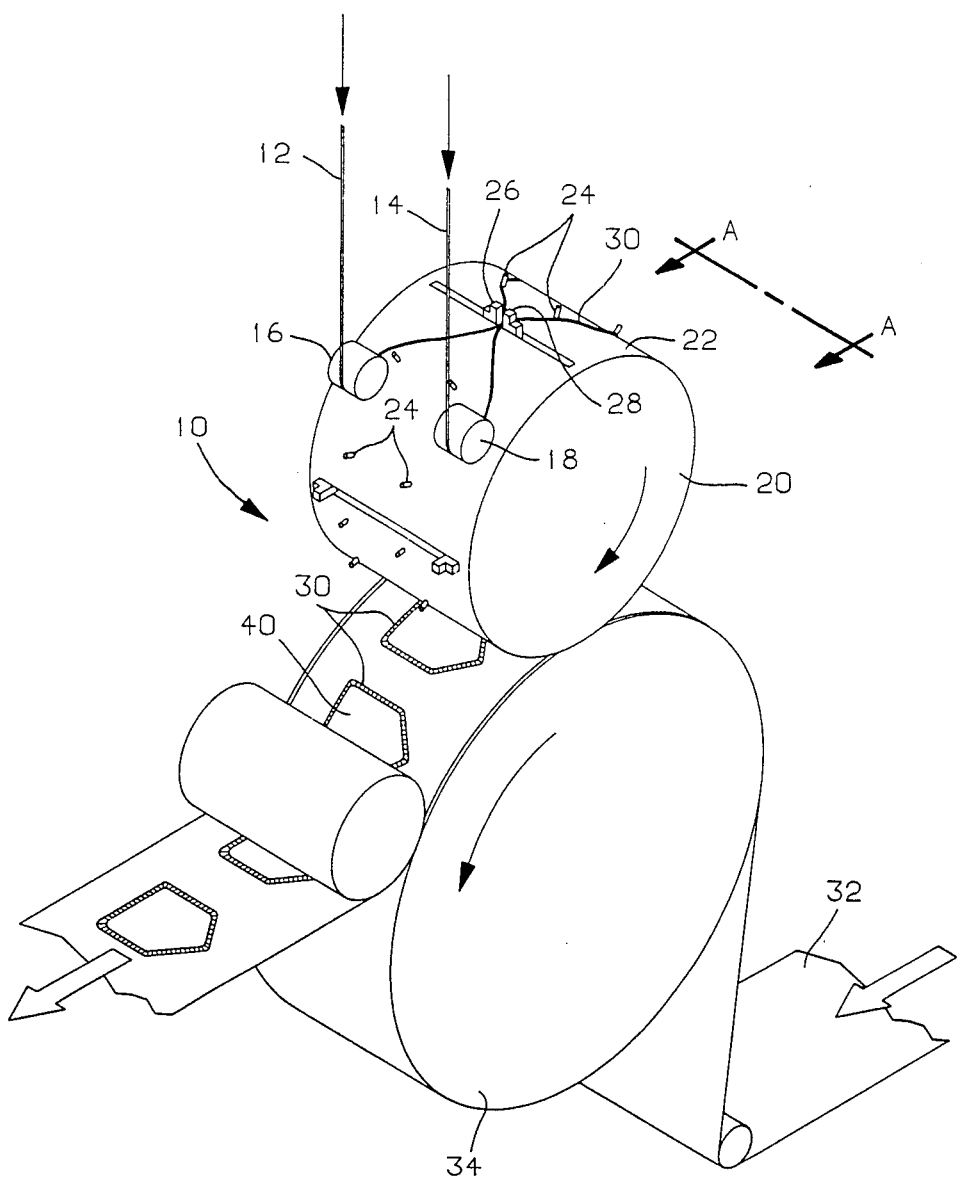
FIG. 1 is a perspective view of an apparatus for applying elastic patterns on a substrate and transferring them to a web.
Figure 2:
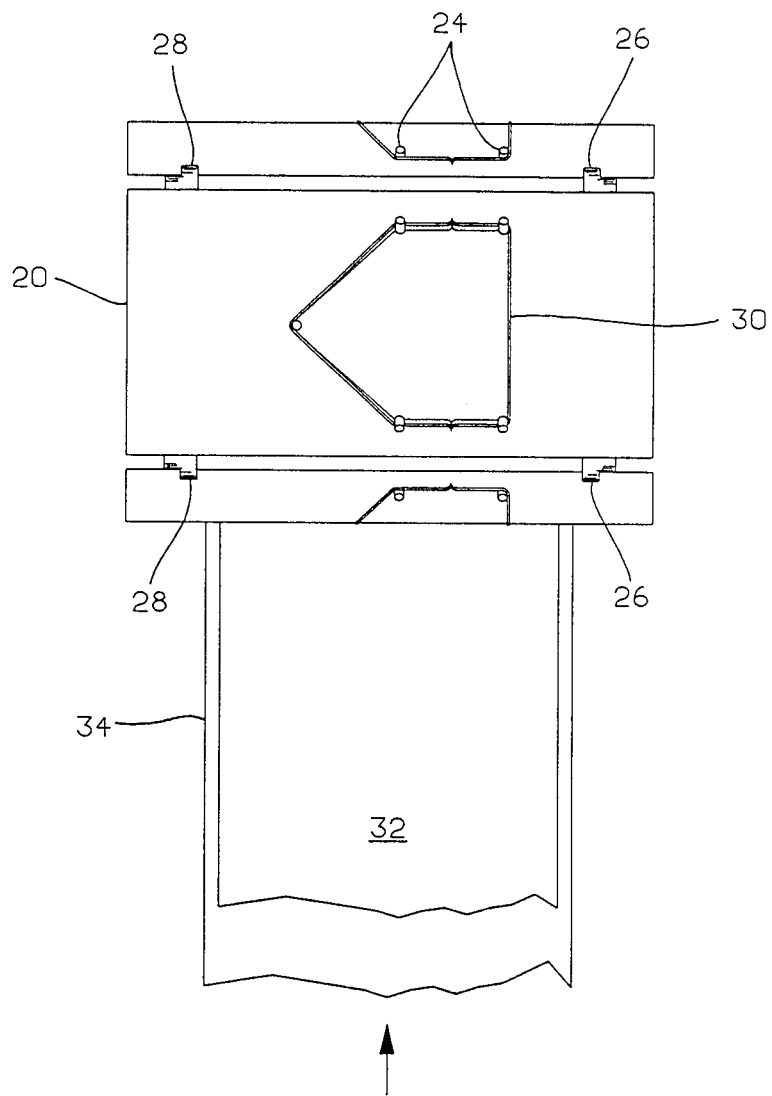
FIG. 2 is a view of the apparatus of FIG. 1 from direction A—A of FIG. 1.

The apparatus 10 of FIGS. 1 and 2 applies contoured self-adhering elastic in accordance with the invention. The elastic strips 12 and 14 are fed to the apparatus in stretched condition. These strips 12 and 14 are fed beneath rollers 16 and 18 that ride near the surface 22 of drum 20. The surface 22 is provided with a release material such as silicone rubber. The rollers place the elastic 14 and 12 on the surface 22 of the drum on each side of the pattern of retractable pins 24. As the drum rotates the elastic moves away from the applicator rolls 16 and 18 and begins to wrap the circumference of the drum 20. The elastic is grasped and brought together by the clamp devices 26 and 28. One set of clamping devices is ahead of each pattern while the other is behind the pattern. By ahead it is intended to mean the leading clamps based on direction of movement and behind are the following clamps based on direction of movement of the elastic. The major stretch of the self-adhering elastic is applied to the elastic prior to its being applied to the drum 20 although the actions of clamps 26 and 28 may also provide additional stretch. One of the clamping devices 26 and 28 also has a heated knife to sever the strands in the bonded section after clamping, and the joined strands spring around the pins 24 as loop or ring 30. The loop of elastic 30 moves with rotation of the drum towards the web 12 carried by drum 34. As the drum 20 rotates the clamping devices 28 and 26 are retracted so that they are outside of the area of contact of applicator drum 20 with the web-carrying drum 34. As drum 20 contacts the web 32, the pins 24 are forced to retreat by the pressure of the nip formed by drums 20 and 34, and the elastic is adhesively transferred by pressure at the nip to the web 32. The web 32 bearing the elastic loops 30 is then drawn from drum 34 for transport to another area (not shown) for further forming into products.

The web 32 with the loops may be further formed by having the polygonal generally circular elasticized area cut from the web to form articles such as shower caps or operating-room caps. In another preferred embodiment the center portion 40 could be severed and removed, and a sheet bearing the elasticized area formed into a garment with the elasticized area at the wrists, waist or legs.

Figure 3:
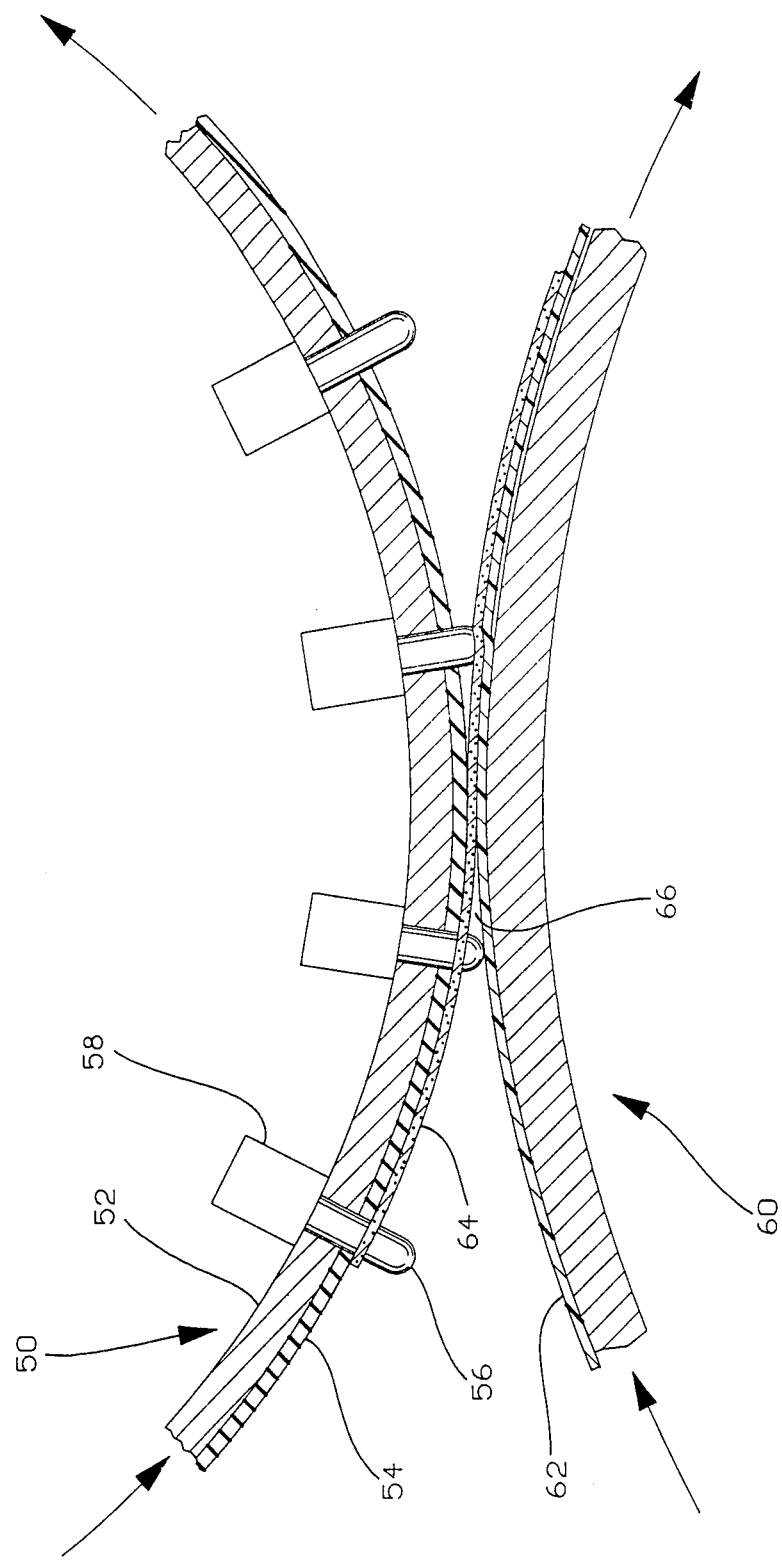
FIG. 3 is a cross-sectional view showing pin position at the time of elastic transfer from the elastic to the web.

FIG. 3 illustrates in cross section a transfer in accordance with the invention. In FIG. 3 the appicator or pin drum 50 is formed with shell 52 over which has been placed a silicone rubber or other release layer 54. The pins 56 are mounted in a spring-loaded base 58. The base 58 provides continuous outward pressure for the pins 56. As drum 50 is rotated it comes into close proximity to the receiving or forming drum 60 bearing web 62. The gap between the drums is adjusted to provide pressure to cause adhesion of the elastic to the web without undue deformation of the elastic. Drum 60 bearing web 62 contacts pins 56 causing them to retract. The pressure of the nip 66 causes the self-adhering elastic 64 to transfer to the web 62. As is apparent, the system allows exact placement of the elastic in the pattern corresponding to the outer edges of the pattern of pins 56. The drum 60 may be provided with means to apply a vacuum beneath web 62 in order to cause it to adhere to drum 60.

Figure 4:
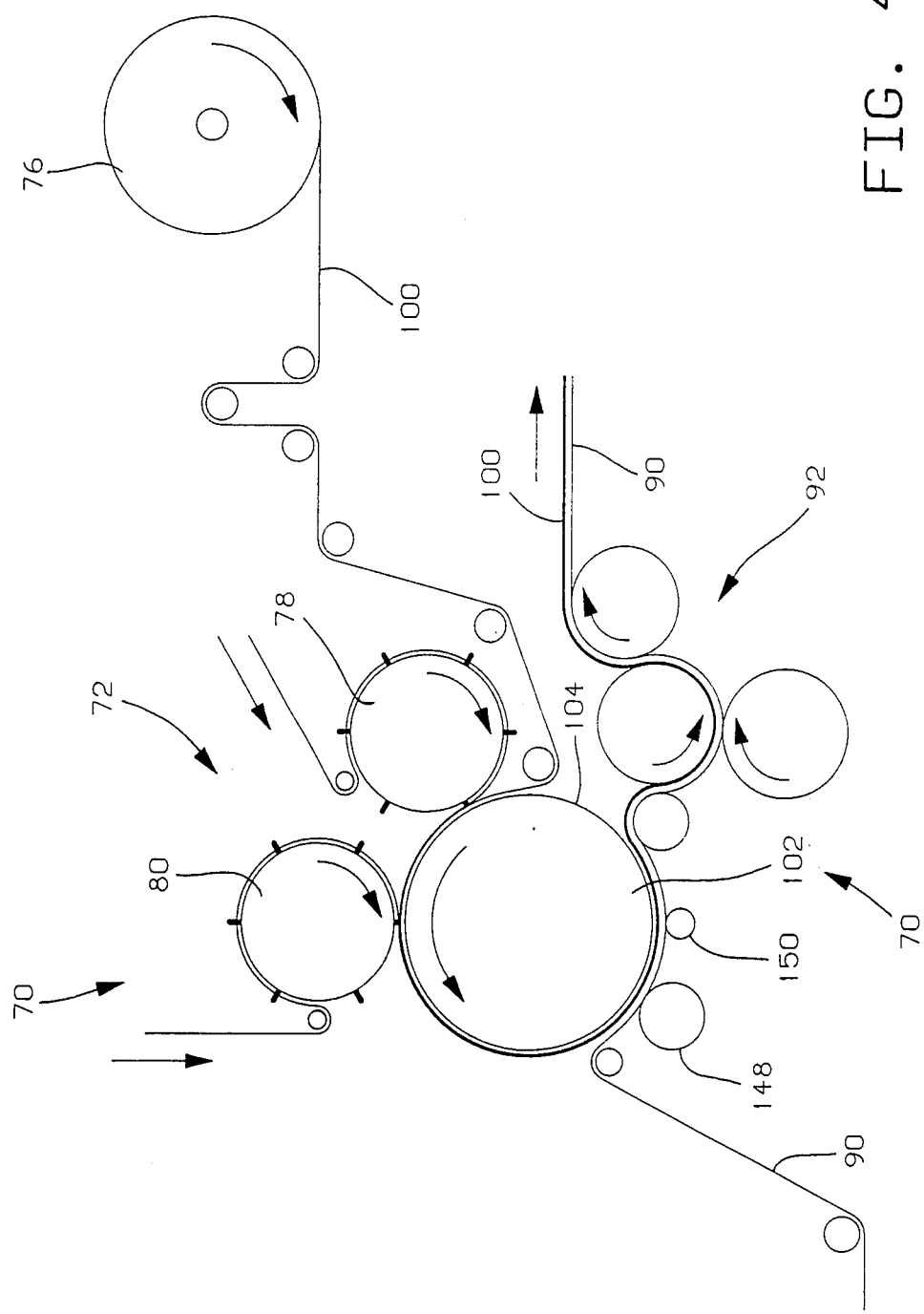
FIG. 4 is a schematic of an apparatus utilizing the retractable pin elastic applicator to form concentric loops of elastic.
Figure 5:
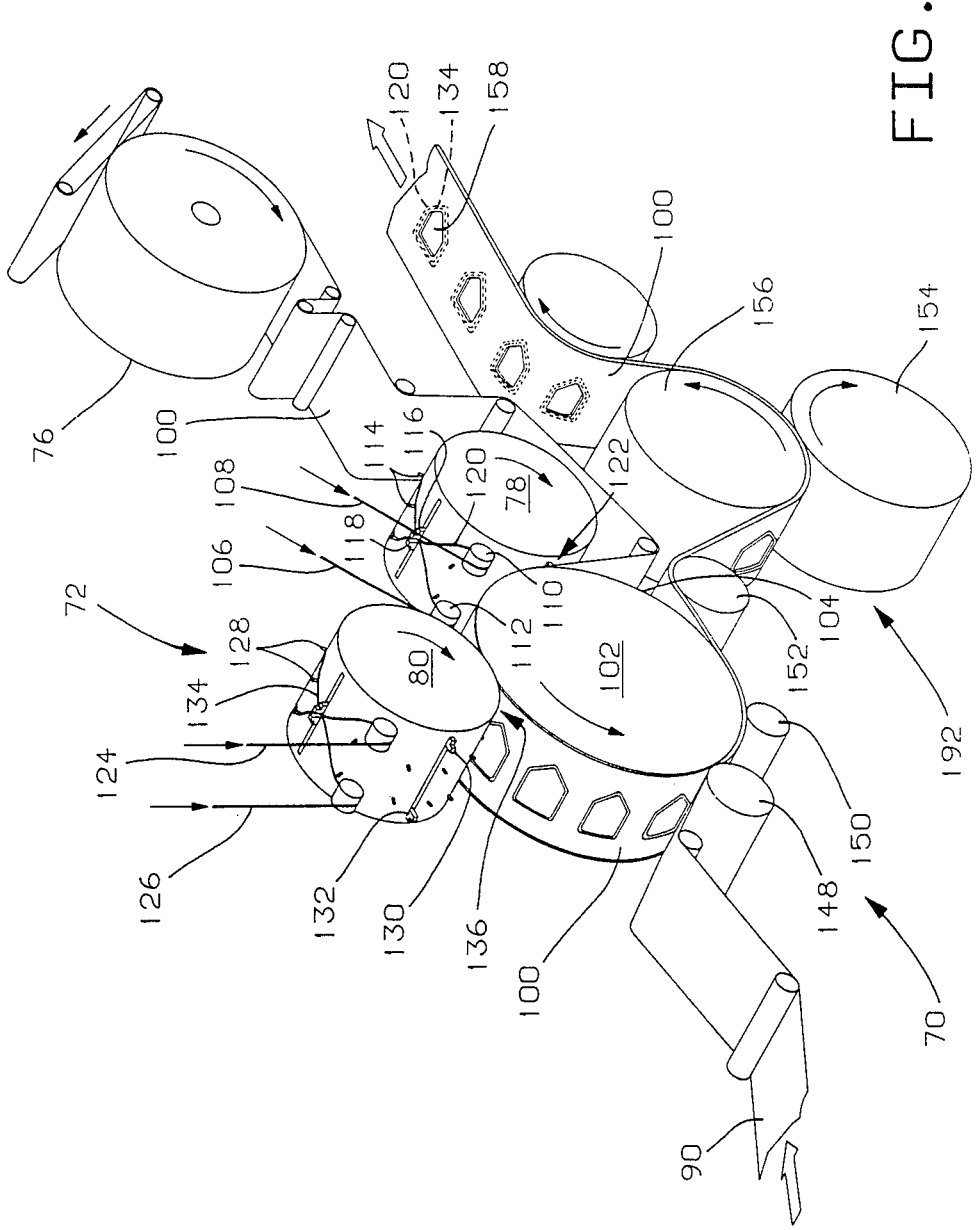
FIG. 5 is a perspective view of the apparatus of FIG. 4.
Figure 6:
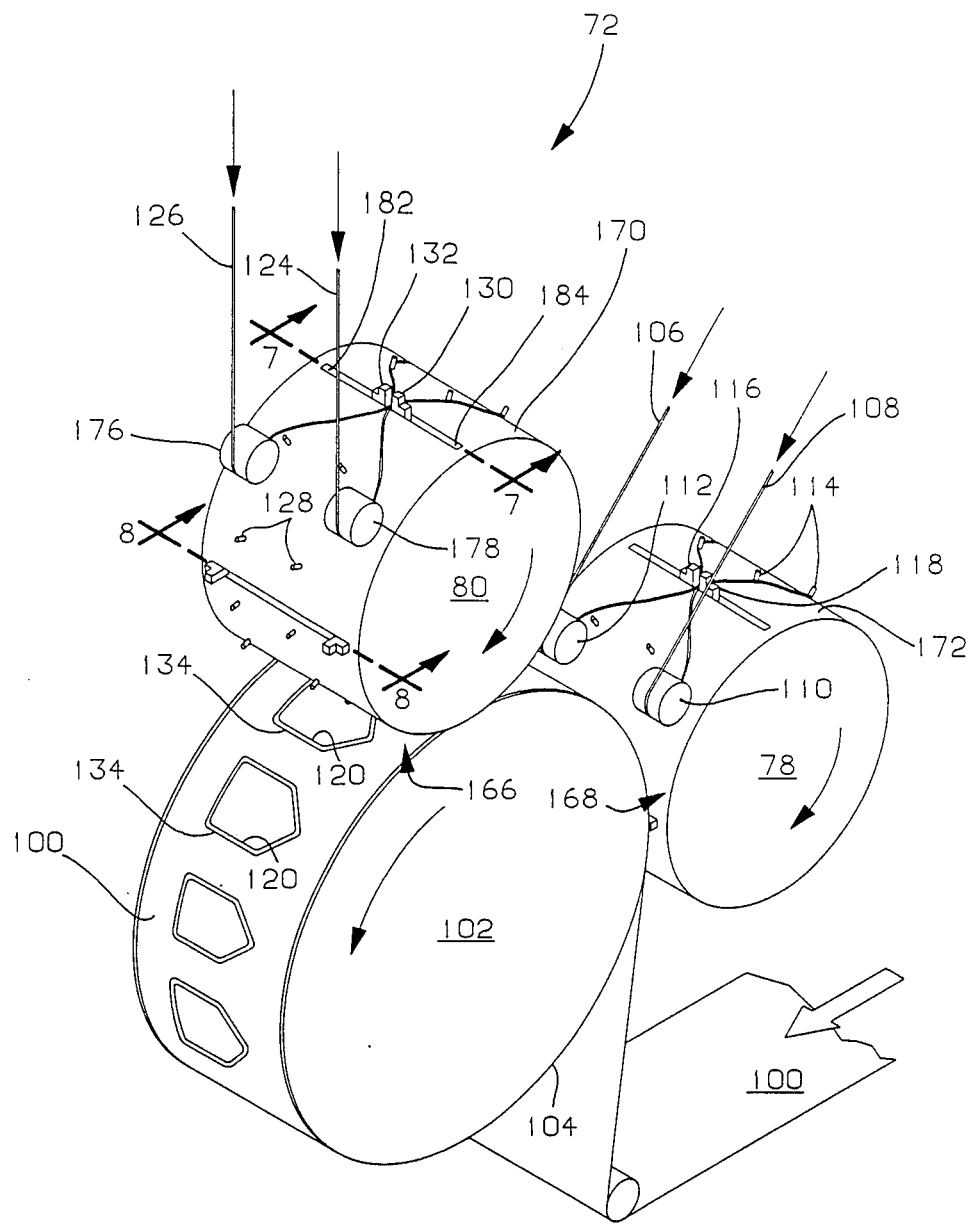
FIG. 6 is a perspective view of the pin drum applicator in the apparatus of FIG. 4.

Illustrated in FIGS. 4, 5 and 6 is apparatus that may be used to form a web with loops of elastic utilizing the retractable pin application device for elastic placement. The web has accurately placed dual loops of elastic. The elasticized web formed by the device illustrated may be formed into an absorbent garment such as an incontinent garment or diaper, such as disclosed in Ser. No. 690,351 filed Jan. 10, 1985 by Heran et al. entitled DISPOSABLE UNDERPANTS SUCH AS INFANT'S TRAINING PANTS AND THE LIKE, now U.S. Pat. No. 4,641,381, Ser. No. 690,349 filed Jan. 10, 1985—Ales et al. entitled DISPOSABLE GARMENTS WITH MULTIPLE STRAND ELASTICIZED OPENINGS, now U.S. Pat. No. 4,642,819, or Ser. No. 740,135 filed May 31, 1985 by Strohbeen et al. entitled DISPOSABLE UNDERPANTS HAVING DISCRETE OUTER SEALS, now U.S. Pat. No. 4,610,681. The accurate placement of multiple contoured elastic at garment openings has advantages in sealing against leakage, lessening of skin reddening, and improving appearance of disposable garments.

As illustrated in FIGS. 4 and 5, the elasticized web-forming apparatus 70 is composed of elastic application apparatus 72, a source of web material 76, and pin application devices 78 and 80 for application of two rings of elastic. The web bearing loops of elastic to be formed into a garment further may be provided with a facing 90. the apparatus of 92 cuts the holes from within the elastic loops. The cut holes may be removed by vacuum withdrawal (not shown). The product web then may be further treated to form elasticized garments and other articles. The above-cited Ser. No. 740,135—Strohbeen et al. filed May 31, 1985, now U.S. Pat. No. 4,610,681, hereby incorporated by reference, discloses a method of sealing the side seals of a garment. As is apparent, a variety of garments and elasticized products could be formed by the pin applicator device of the invention that may be utilized to put contoured elastics on a variety of substrates.

The operation of the apparatus 70 will be described with reference to FIGS. 4, 5 and 6. The backing sheet for the garment is supplied from source 76 as sheet 100. Sheet 100 is fed to the forming drum 102. Forming drum 102 is preferably provided with a vacuum source such that the web 100 is securely adhered thereto by the vacuum being drawn through a series of holes in the outer surface 104 of the drum. Instead of vacuum it is possible that the web would be held in place by needles piercing the material at the edge or by a tenter frame. It is also possible that the web not be secured to the drum by vacuum but held in place by winding tension and friction with the drum surface. The web 100 adhered to drum 102 then passes beneath the first pin applicator roll 78 to which is fed in a straight line two strips of stretched self-adhering elastic 106 and 108. These strips of elastic are applied to the rim 78 below rollers 110 and 112 and are formed in rings around pins 114 by cutting and adhering devices 116 and 118. When the rings of elastic 120 pass through the nip 122 the pins 114 are retracted, and the elastic 120 is adhered to web 100. The web 100 bearing ring 120 is then moved as drum 102 rotates beneath the second pin drum roll 80. In a similar manner pin drum roll 80 applies two strips of self-adhering elastic 124 and 126 to the drum 80 where it is applied around pins 128 with sealing together of the strips 124 and 126 by the nipping/cutting apparatus 130 and 132. Rings of elastic 134 are formed which at nip 136 are transferred to sheet 100. As illustrated, the rings 134 are somewhat larger than the previously-formed ring 120 such that they form an outer circumferential ring around the earlier place ring 120. The rotation of the product-forming drum 102 then brings the web bearing the double ring of elastics 134 and 120 to the point of application of sheet 90 that covers the exposed self-adhering elastic so that the web may be handled. The composite then is formed as the sheet 90 is adhered to the exposed elastic adhesives by contoured pressure rollers 148 and 150.

The elasticized composite is removed by being drawn over roller 152 and brought to the die cutters 192 composed of rolls 154 and 156. These cutting rolls remove the portion within eastic loops or bands 120 and 134 to leave hole 158. The composite then may be cut into blanks for immediate conversion to articles or may be rolled for later conversion.

FIG. 6 is a detailed view of the pin application devices of 72. It is noted that the rings of elastic 120 and 134 are precisely placed upon the web 100. The ability to perform such exact placement is a particular advantage of the system of the invention. The surface 170 of roller 80 and surface 172 of roller 78 is provided with a release surface that is not adherent to the self-adhesive elastics.

The surface of rollers 176, 178, 110 and 112 that apply the self-adhering elastic to drums 78 and 80 must be a release material for the self-adhering elastic, such as a silicone rubber. Further, it is noted that the bonding and cutting devices 130 and 132 must be retracted to the end portions 182 and 184 of their track prior to the pin applicator drum being brought into contact with the garment-forming drum 102 so that the nipper/cutters are not pressed against drum 102 and damaged.

The devices for holding, fusing and cutting the self-adhering elastics are illustrated in FIGS. 7, 8, 9 and 10. As shown in FIGS. 7 and 9, the bonding and cutting devices or cutter/nippers 190 and 192 are holding the elastic for bonding and cutting to form the separate rings. The elastics 194 and 196 are gathered and brought together as devices 190 and 192 move from edge positions 198 and 200. The cutters are moved by suitable camming devices not shown. As shown in FIG. 9 from the top view, the cutting and fusing device 190 is composed of separate clamping surfaces 202 and 204 that bear against surfaces 206 and 208 to bond the separate ribbons 194 and 196 of self-adhering elastic together. After the areas 202 and 206 and 204 and 208 are brought together, the knife portion 210 passes through the elastic onto anvil 212 and cuts the elastic ribbons 194 and 196. The knife is spring loaded such that it is not applied through the intersection between horns 202 and 204 until these have clamped the elastic under pressure. The nipper/cutter 190 and 192 are then retracted so as to clear the forming drum 102 when the elastic transfer is made and to be in position for bringing together to stretch, bond and cut the strands of elastic that are next applied to pins 128. When the nipper/cutters are separated after cutting, the elastic springs back to elastically grip the pins 128. FIGS. 8 and 10 illustrate the nipper/cutter devices 190 and 192 in spread position with the elastic being contracted around the pins 128 to form a continuous band 216. As the nipper/cutter devices 190 and 192 extend above the surface 220 of the pin applicator roll 222, it is necessary that they be withdrawn to the edges of the roll as shown in FIG. 10 when the roll is in position for transfer of the elastic from upon the pins to a web.

The surface of the pin applicator rolls 22 in FIG. 1 must be covered with a material that is not adherent to the self-adhering adhesive being applied to a web by the pin applicators. The release material typically is somewhat resilient when silicone rubber is used, but is not essential that the surface be both a release surface and resilient in order to function. This surface may be formed of any suitable release material for the elastic adhesive being used. Typical of such release materials are fluorinated hydrocarbons, highly polished ceramics such as silicone carbide, or metals treated with a release oil such as silicone oil. A preferred material is a silicone rubber of 40 to 100 durometers hardness and particularly preferred is the silicone rubber Silastic ® J RTV available from Dow Corning Corporation having a durometer hardness of about 60. The silicone rubber is also preferred as the release surface for the delivery rolls that stretch the self-adherent elastic and apply it to the surface of the drum.

The pins, such as 24, also must have a surface that is nonadherent to the self-adhering elastic. Typical of such surfaces are those listed above for the applicator roll surface. A suitable surface has been found to be a fluorinated hydrocarbon surface of tetrafluoroethylene composition. A most preferred surface is a silicone rubber of 40–100 durometer hardness and of a composition as set forth above for the applicator roll. Further, it is possible that the surface may, if appropriate, have an oil either fed from within or added to the surface periodically. Teflon is a preferred coating for the pins as it has better abrasion-resistant properties. As the pins are periodically pushed into the roll and extended out again abrasion resistant is desirable as the pins may bear against the sides of holes through which they extend. Silicone is a preferred material as it has good release properties from the self-adhering elastics.

The pins are arranged in any suitable configuration or pattern on the applicator drum to result in the elastic being placed in the desired contour. The pins should be in convex pattern so that the stretched elastic will assume the pattern formed by the pins. The pins themselves may extend any suitable distance from the applicator drum. They must extend a suitable distance such that the elastic when it rebounds after being cut does not flip over the top of the pins. A suitable distance for extension of the pins generally is between about ¼ and about ½ inch. A preferred distance for extension has been found to be about ⅜ inches. However, depending upon the size of the elastic band and the diameter of the loop being formed around the pins, the distance may be varied to whatever is effective.

The invention has been described with retraction of spring loaded supports when the applicator drum bearing the support contacts the web. However, it is possible that the pin retraction could be carried out by positive mechanical means such as cams or solenoids in the drum. The spring loaded supports are preferred because they are simple and reliable. If a drum with positive means to extend and withdraw pins was used it would be possible to use one applicator roll to make different products by selective extension and retraction of pins to form different polygonal patterns. Further, concentric loops could be formed by retracting the outer pattern of pins, forming the inner loops, then extending pins of the outer pattern and forming the outer loops of elastic around the outer pins. The concentric loops could then be simultaneously transferred.

The pins or supports may be any cross-sectional shape that results in a suitable product. It has been found that the pins are best of generally circular cross section as these do not result in premature release of the elastic when the pins reach the nip.

Figure 11:
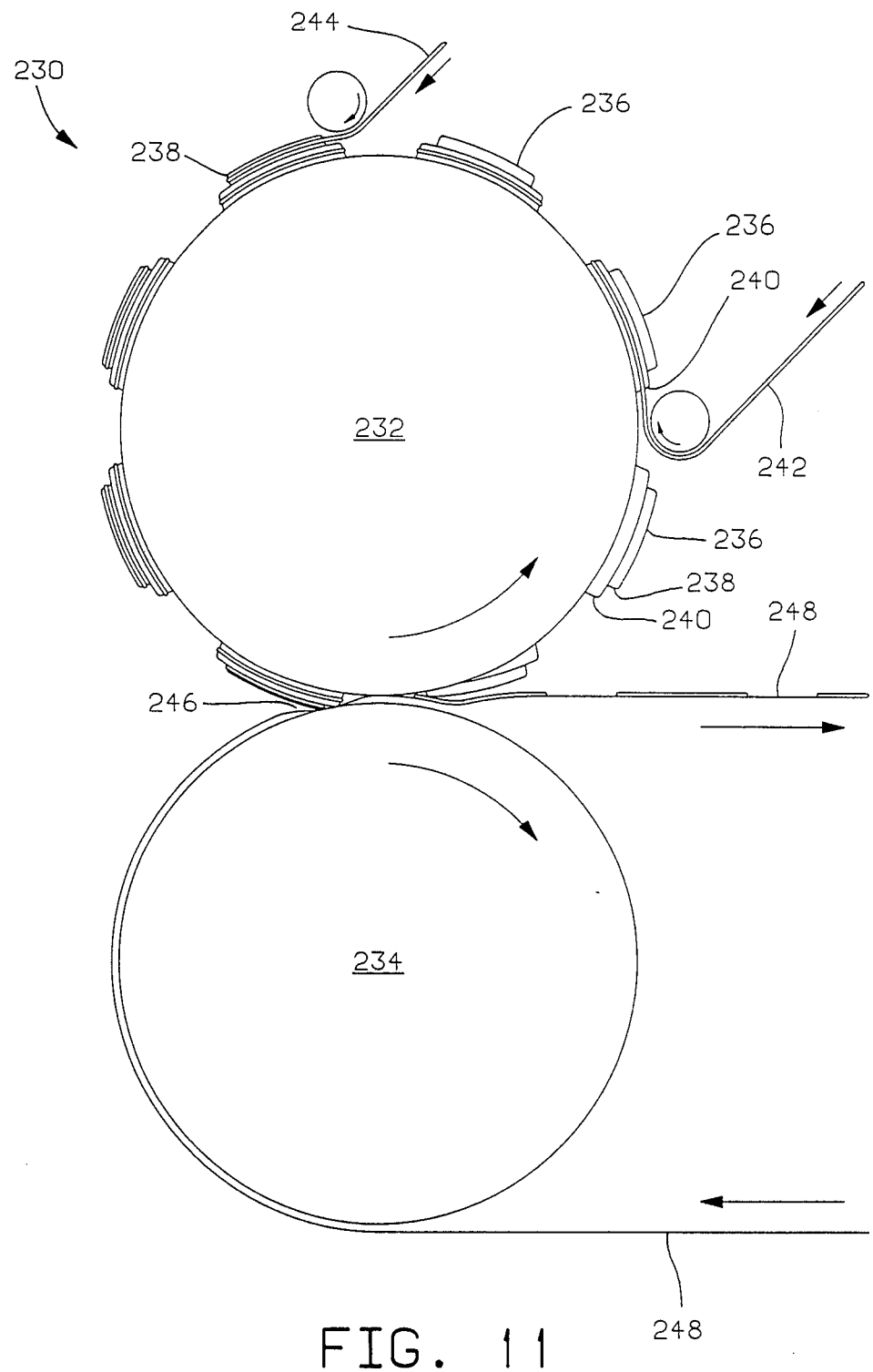
FIG. 11 is an illustration of apparatus for transferring loops of self-adhering elastic utilizing male and female molds.

FIGS. 11–22 illustrate alternative embodiments of the invention for application of self-adhering elastic in nonlinear shapes onto a web substrate. In FIG. 11 the apparatus 230 is comprised of an applicator drum 232 and a vacuum web-carrying drum 234. Application drum 232 is provided with a series of male die blocks 236 having two surfaces 238 and 240, generally perpendicular to the drum surface, around which the elastic is wrapped, by means not shown. Eastic 242 and 244 are applied to the applicator roll 232 with elastic loop 242 being placed around the lower receiving area 240 and elastic loop 244 placed around the upper receiving area 238. The applicator roll 323 is brought in to corotating contact with the vacuum receiving roll 234 at 246. The roll 234 is provided a web material 248 that has been drawn thereto by vacuum. The male molds 236 deflate and deform at nip 246 to effect transfer of the elastics 238 and 240 to the web 248 by pressure contact.

FIGS. 12 and 13 illustrate the male mold 236 of roll 232. The molds may be air inflated from a source of compressed air 252. The inflatable mold will allow roll 232 to better conform to receiving roll 234, and allow the inflation pressure to aid transfer of the elastics 242 and 244 to the receiving web 248. It is also possible that a deformable or inflatable male mold could be brought into contact with a matching female mold and transfer accomplished by deforming the male mold so that the elastic loops on the mold are brought into contact with a web adhered to a female mold carried on a vacuum roll. As illustrated in FIG. 11, the male mold 236 acts somewhat like a large single pin around which the elastic is wrapped.

Figure 16:
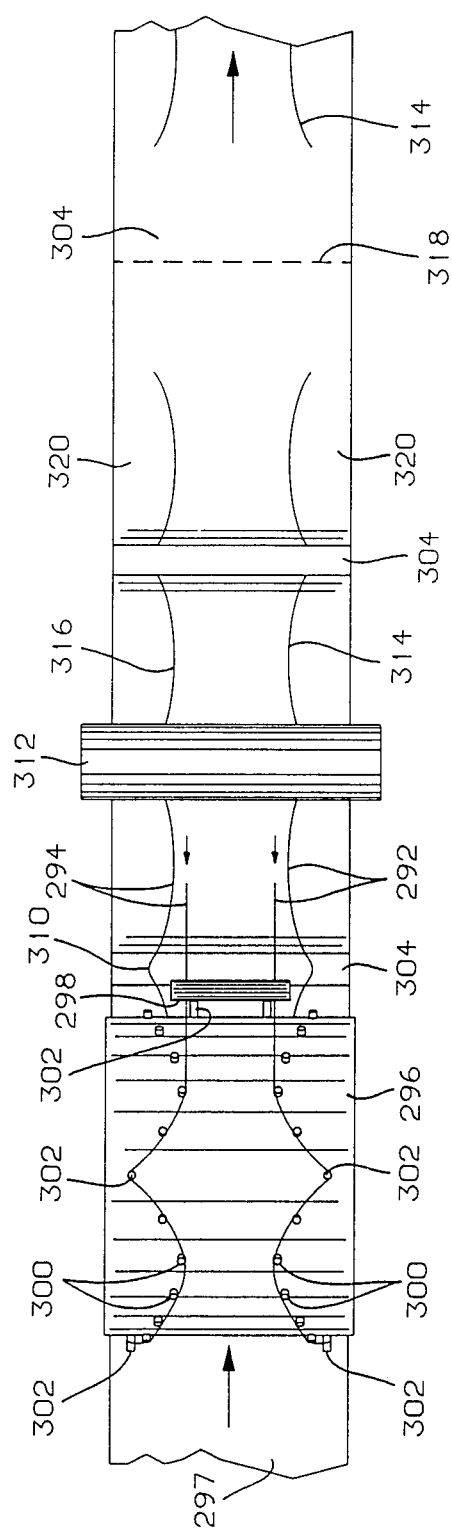
FIGS. 16 and 17 illustrate apparatus for forming contoured shaped elastic utilizing movable posts to contour the elastic.

FIG. 14 illustrates another alternate embodiment utilizing transfer of elastic ribbons on a male mold. In FIG. 14 the male mold 260 is solid while the receiving mold 262 is flexible and may have air or hydraulic pressure 264 applied thereto. The web material 266 is pressed by the flexible mold 262 against the elastics 268 and 270. FIG. 16 is a further alternative embodiment utilizing male and female rolls. In FIG. 15 the male mold and female mold 282 are solid and have elastics 284 and 286 applied thereto. The transfer of self-adhering elastic 284 and 286 to the web 288 is affected by pressure contact of the mold numbers 282 and 283.

Figure 17:
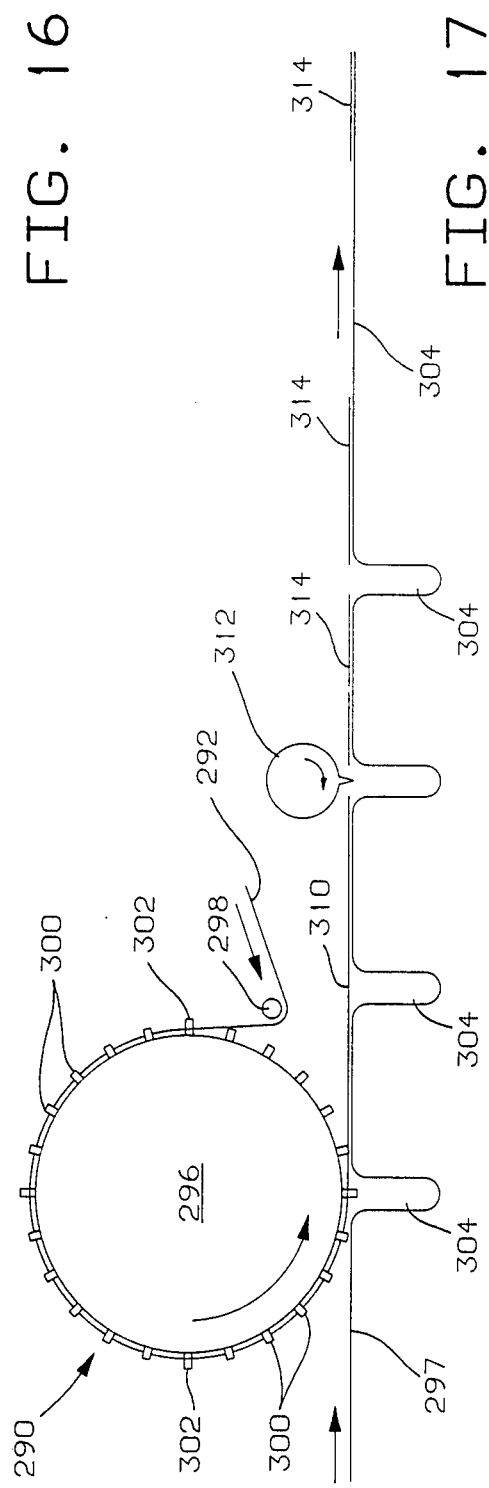

FIGS. 16 and 17 illustrate another embodiment of the invention utilizing retractable pins for shaping the self-adhering elastic. As is illustrated in FIGS. 16 and 17, the apparatus 290 is capable of applying contoured elastics 292 and 294 to a web of material 297. The elastics 292 and 294 are brought to the forming roll 296 by straight line feeding of the elastic 292 around guide roll 298. The applicator roll 296 is provided with a series of pins 300 fixed in location but retractable under pressure into roll 296. The elastics 292 and 294 are brought into contact with the convex arrangement of fixed location pins 300 by movement of movable pins 302. Pins 302 move the elastic outward to the edge of roll 296 and thereby stretch it and bring it into contact with the fixed location pins 300. Transfer to web 297 is effected while web 297 has an open-downward fold 304 formed therein. The making of such downward folds prior to formation of elasticized garments is known in the diaper formation process and disclosed in U.S. Pat. No. 4,227,952—Sabee. The downward-folded portion 304 in the formation of diapers is the part that forms the back and front of the diaper while the contoured elastic would form the leg elastic portions. The portion of elastic 310 spanning fold 304 is severed by cutting roll 312 to form the contoured leg portions 314 and 316. When the fold 304 is opened the web may be cut such as at phantom line 318 to form separate garments with elasticized legs. Further, the flap portion 320 within the elastic legs may be cut out if desired, by means not known.

Figure 18:
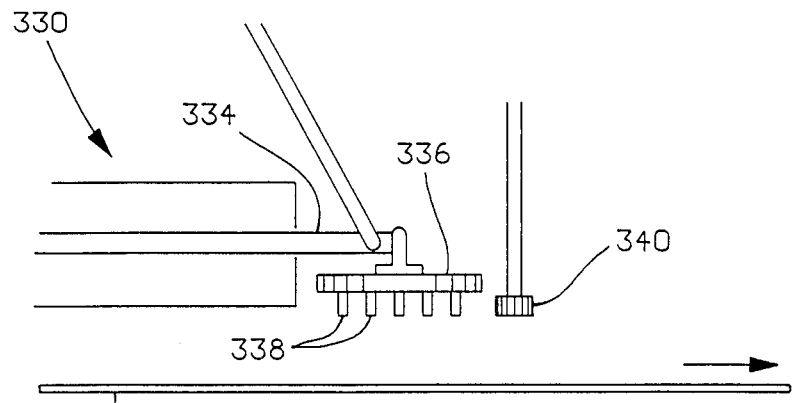
FIGS. 18–20 illustrate reciprocating apparatus for intermittent application of loops of elastic to a moving continuous web.
Figure 19:
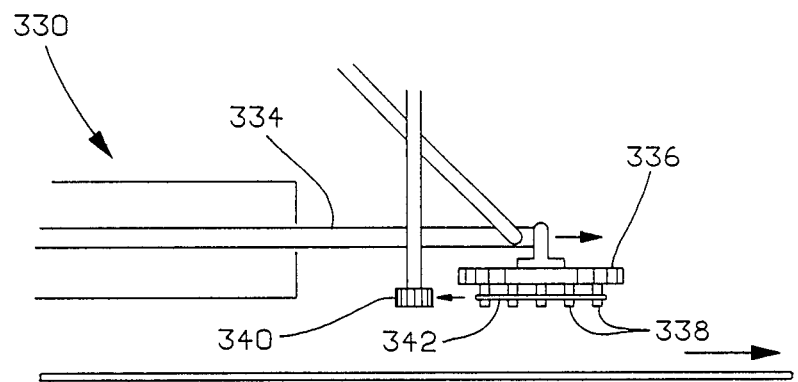
Figure 20:
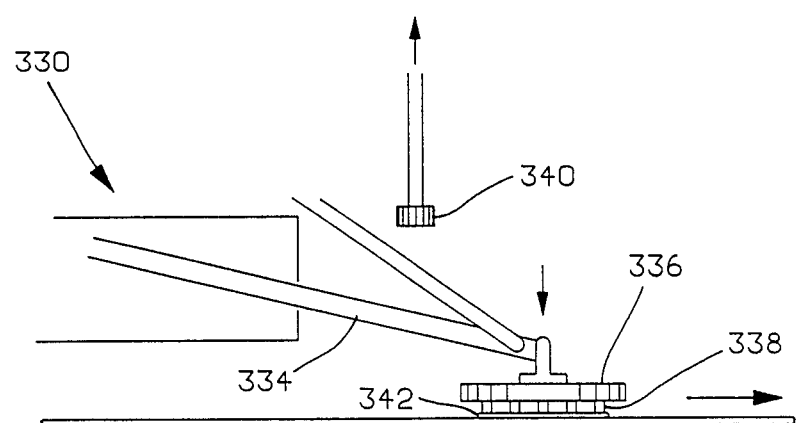

FIGS. 18–20 are a schematic illustration of another method and apparatus by which the retractable pin elastic applicator may be formed. Elastic applicator device 330 is designed to provide intermittent application of a strip of elastic to a web 332 passing below the applicator 330. The applicator is provided with an arm 334 that is movable up, to the left and downward. The arm is provided with a retractable pin applicator 336 having retractable pins 338. Stretched elastic placement device 340 provides means for placing a loop of stretched elastic 342 around pins 338. The elastic is moved by moving the applicator device 336 past the loop-forming means 340 to position shown in FIG. 19. The pin applicator 336 is then brought into contact with the moving web 332 such that it is moving at the same speed as the web 332 during the time of contact for pin retraction and transfer. The arm 334 is then raised and returned to the starting position of FIG. 18 prior to being recycled through the loop formation and elastic application to the substrate steps of FIGS. 19 and 20 in a reciprocating motion.

The self-adherent elastic may be formed of any elastic material that has adherent properties. Further, as the term self-adherent is used therein it also includes elastic materials that have been caused to be self-adherent by being coated with adhesive such as by dipping into an adhesive material. Further, the invention could be utilized as an equivalent process or apparatus with nonself-adhering elastics if the nonadherent elastics were being transferred to a surface covered with adhesive. Further it could be used to transfer decorative areas onto a substrate by heating and fusing of ribbons of decorative material at the interface of application to a substrate.

For use in the preferred process of the invention for application of elastics to a garment, the self-adhering elastics such as disclosed in U.S. Pat. Nos. 4,418,123 and its parent application 4,259,220—Bunnelle et al., both incorporated herein, have been found to be particularly preferred. This material is a block copolymer having glassy end blocks and amorphous midblocks. Further, the resin has a tackifying resin associated with the midblock. There is also a resin associated with the glassy vinylarene end blocks such as low molecular weight, alpha-methyl styrene-vinyl toluene synthetic copolymers or coumaroneindenes. However, other self-adhering elastics could be utilized.

The self-adhering elastic strip may be any suitable cross section for use in the invention. It is considered that strips in the shape of ribbons, ropes or more complex cross-sections may be utilized. It is preferred that the cross-sectional aspect ratio be between about 1 to 1 and 1 to 2 in order that the material not be deformed when forming the patterned loop.

The web to which the elastic is adhered may be any suitable flexible material that is adherable to the self-adherent elastic. The material may be a fabric or a liquid impermeable polypropylene film or polyethylene polymer sheet such as used for diapers and incontinent garments. The web also could be a paper or spunbonded fabric or composite of film and nonwoven fabric. The choice of the base material is dependent upon the article to be formed.

The invention has been illustrated with formation of an elasticized web. The web may be used for forming an incontinent garment such as used for diapers, training pants or incontinent adults, the method of applying contoured elastic could be used in any desired manner to form any desired article including those such as catamenial devices. The elasticized web could be used for forming elastic wrists for disposable garments such as used for radiation protection. It could be used for forming elastic necks or anklets in such garments. Another use would be formation of caps such as used for shower caps or for sterile purposes in medical use or in manufacture of dust-free or sterile articles. Elasticized materials may be used in formation of covers for bowls. Further, elasticized tablecloths or openings for bags could be formed or garments may be partially constructed on the vacuum drum carrying the web by placing absorbent materials onto the web after the elastic loops have been transferred to the drum. These and other uses will be apparent to one of ordinary skill in the art and are intended to be included by the claims attached.

What is claimed is:

1. Apparatus for bonding elastic to a substrate, comprising: self-adhering elastic, means to apply said loops in a stretched condition around at least one support, means to bring said support into contact with a web, means to cause relative movement between said support and said web and thereby bring said elastic into adhering contact with said web.
   (A) at least one convex polygonal pattern of supports,
   (B) means to form loops of self-adhering elastic and comprising
      (i) means to feed two strands of stretched self-adhering elastic such that one strand is on each side of said pattern of supports
      (ii) means to bond the strands to each other ahead and behind said pattern of supports
      (iii) means to sever the bonded strands in the bonded areas to form a loop of stretched self-adhering elastic around said pattern of supports
   (C) means to bring said pattern of supports into contact with a web, and
   (D) means to cause relative movement between said pattern of supports and the web to bring the loop of stretched self-adhering elastic into adhering contact with the web.

2. The apparatus of claim 1 wherein there is a plurality of means to form loops mounted on a rotating applicator drum.

3. The apparatus of claim 2 wherein there is provided a plurality of applicator drums.

4. The apparatus of claim 3 wherein said plurality of applicator drums apply said elastic loops in concentric relationship on said web.

5. The apparatus of claim 4 wherein said web is adhered by vacuum means to a rotating forming drum and the applicator drums are provided with means to rotate them into contact with a rotating forming drum carrying said web.

6. The apparatus of claim 5 wherein said forming drum and said applicator drum form a nip, and said supports are withdrawn by the pressure applied to said supports by the narrowing of said nip.

7. The apparatus of claim 2 wherein said applicator drums are provided with a surface nonadherent to said self-adherent elastic.

8. The apparatus of claim 1 wherein said supports comprise pins of generally circular cross section.

9. The apparatus of 1 wherein said support comprises a deformable mold.

10. The apparatus of claim 9 wherein said mold is inflatable.

11. Apparatus for forming and applying a closed-loop of elongate material to a substrate, comprising:
    a supporting surface,
    means for supplying two lengths of an elongated material to said supporting surface,
    means for attaching the two lengths of elongate material into a closed-loop on said supporting surface,
    means for delivering a substrate to said supporting surface, and
    means for releasing the closed-loop of elongate material from said supporting surface onto the substrate.

12. The apparatus of claim 11
    wherein said attaching means attaches the first and the second lengths of elongate material to each other on said supporting surface, and further comprises means for serving the first and the second lengths of elongate material at their areas of attachment, thereby forming a closed-loop of elongate material.

13. The apparatus of claim 12 further comprising a second supporting surface, and
    wherein said supply means supplies a third length of elongate material and a fourth length of elongate material to said second supporting surface, and
    further comprising a second attaching means for attaching the third and the fourth lengths of elongate material into a second closed loop on said second supporting surface, and means for severing the third and the fourth lengths of elongate material at their areas of attachment, and
    second means for releasing the second closed-loop of elongate material from said second supporting surface onto the substrate.

14. The apparatus of claim 13
    wherein one of said attaching means forms its respective closed-loop of elongate material with a perimetrical length greater than the perimetrical length of the other closed-loop of elongate material, and
    wherein said second releasing means releases its second closed-loop of elongate material onto the substrate such that the closed-loop of elongate material are generally concentrically disposed on the substrate.

15. The apparatus of claim 11 wherein said supporting surface comprises a plurality of retractable pin members.

16. The apparatus of claim 11 wherein said supporting surface comprises a deformable mold.

17. The apparatus of claim 11 wherein said supporting surface is convexly shaped.

* * * * *

UNITED STATES PATENT AND TRADEMARK OFFICE
CERTIFICATE OF CORRECTION

PATENT NO. : 4,726,873

DATED : February 23, 1988

INVENTOR(S) : Thomas M. Ales, et al.

It is certified that error appears in the above-identified patent and that said Letters Patent is hereby corrected as shown below:

Column 3, line 17, delete "12" and substitute therefor --32--.
Column 4, line 68, delete "eastic" and substitute therefor --elastic--.
Column 6, line 19, delete "resistant" and substitute therefor --resistance--.
Column 7, line 29, delete "FIG. 16" and substitute therefor --FIG. 15--.
Column 7, line 63, delete "known" and substitute therefor --shown--.

In claim 1, Column 9, line 13, delete ",".
In claim 1, Column 9, line 14, delete ": self-adhering elastic, means to apply said loops in a stretched condition around at least one support, means to bring said support into contact with a web means to cause relative movement between said support and said web, and thereby bring said elastic into adhering contact with said web.".

UNITED STATES PATENT AND TRADEMARK OFFICE
CERTIFICATE OF CORRECTION

PATENT NO. : 4,726,873

DATED : February 23, 1988

INVENTOR(S) : Thomas M. Ales, et al.

It is certified that error appears in the above-identified patent and that said Letters Patent is hereby corrected as shown below:

In claim 9, Column 10, line 3, after the word "of" and prior to "1", insert the following word --claim--.
In claim 12, Column 10, line 21, delete "comprises" and substitute therefor --comprising--.
In claim 12, Column 10, line 22, delete "serving" and substitute therefor --severing--.
In claim 14, Column 10, line 47, delete "closed-loop" and substitute therefor --closed-loops--.

Signed and Sealed this

Fifth Day of September, 1989

*Attest:*

*Attesting Officer*

DONALD J. QUIGG

*Commissioner of Patents and Trademarks*